(12) United States Patent
Sanchez Garcia

(10) Patent No.: US 11,752,310 B2
(45) Date of Patent: Sep. 12, 2023

(54) PERFUSION BALLOON WITH A SELECTIVELY ACTUATABLE VALVE

(71) Applicant: C.R. Bard, Inc., Tempe, AZ (US)

(72) Inventor: Edgar Sanchez Garcia, Tempe, AZ (US)

(73) Assignee: C.R. BARD, INC., Franklin Lakes, NJ (US)

( * ) Notice: Subject to any disclaimer, the term of this patent is extended or adjusted under 35 U.S.C. 154(b) by 285 days.

(21) Appl. No.: 15/772,850

(22) PCT Filed: Nov. 6, 2015

(86) PCT No.: PCT/US2015/059473
§ 371 (c)(1),
(2) Date: May 2, 2018

(87) PCT Pub. No.: WO2017/078733
PCT Pub. Date: May 11, 2017

(65) Prior Publication Data
US 2018/0318560 A1  Nov. 8, 2018

(51) Int. Cl.
*A61M 25/10* (2013.01)
(52) U.S. Cl.
CPC . *A61M 25/1002* (2013.01); *A61M 2025/1013* (2013.01); *A61M 2025/1097* (2013.01); *A61M 2210/125* (2013.01)
(58) Field of Classification Search
CPC ..... A61B 2017/00783; A61M 25/1011; A61M 2025/1015; A61M 2025/1072; A61M 2025/1097; A61M 2210/125
See application file for complete search history.

(56) References Cited

U.S. PATENT DOCUMENTS

| 4,983,167 | A | 1/1991 | Sahota |
| 5,181,911 | A | 1/1993 | Shturman |
| 5,226,888 | A | 7/1993 | Arney |
| 5,360,403 | A | 11/1994 | Mische |
| 5,470,314 | A | 11/1995 | Walinsky |
| 5,554,119 | A | 9/1996 | Harrison |
| 6,045,531 | A | 4/2000 | Davis |

(Continued)

FOREIGN PATENT DOCUMENTS

| CN | 103476451 B | 10/2016 |
| JP | H07509160 A | 10/1995 |

(Continued)

*Primary Examiner* — Thomas McEvoy
(74) *Attorney, Agent, or Firm* — Dickinson Wright PLLC; Andrew D. Dorisio

(57) ABSTRACT

An apparatus for performing a medical procedure and, in particular, an aortic valvuloplasty, in a vessel for transmitting a flow of fluid includes a first inflatable balloon, such a perfusion balloon with a plurality of cells in a single cross-section of the balloon for permitting the fluid flow in the vessel. An inflatable valve, which may take the form of a second inflatable balloon, may be provided for controlling the fluid, flow through the first balloon when inflated. Through selective movement of the second balloon when inflated via the flow rhythms created by the beating heart, a one way valve results that can be used to mimic the natural flow created by the valve under treatment.

20 Claims, 4 Drawing Sheets

(56) References Cited

U.S. PATENT DOCUMENTS

| | | | |
|---|---|---|---|
| 2005/0137688 A1* | 6/2005 | Salahieh | A61F 2/2418 623/2.11 |
| 2007/0038292 A1* | 2/2007 | Danielpour | A61F 2/82 623/1.42 |
| 2008/0177127 A1 | 7/2008 | Allan et al. | |
| 2009/0088836 A1* | 4/2009 | Bishop | A61M 29/02 606/192 |
| 2009/0105641 A1 | 4/2009 | Nissl | |
| 2011/0238105 A1 | 9/2011 | Gelbart et al. | |
| 2011/0282369 A1* | 11/2011 | Krolik | A61B 17/320725 606/198 |
| 2012/0209375 A1 | 8/2012 | Madrid et al. | |
| 2015/0250481 A1* | 9/2015 | Chobotov | A61F 2/954 623/1.12 |
| 2015/0272732 A1 | 10/2015 | Tilson et al. | |

FOREIGN PATENT DOCUMENTS

| | | |
|---|---|---|
| JP | 2007516055 A | 6/2007 |
| WO | 9402193 A1 | 2/1994 |
| WO | 2011084500 A2 | 7/2011 |

* cited by examiner

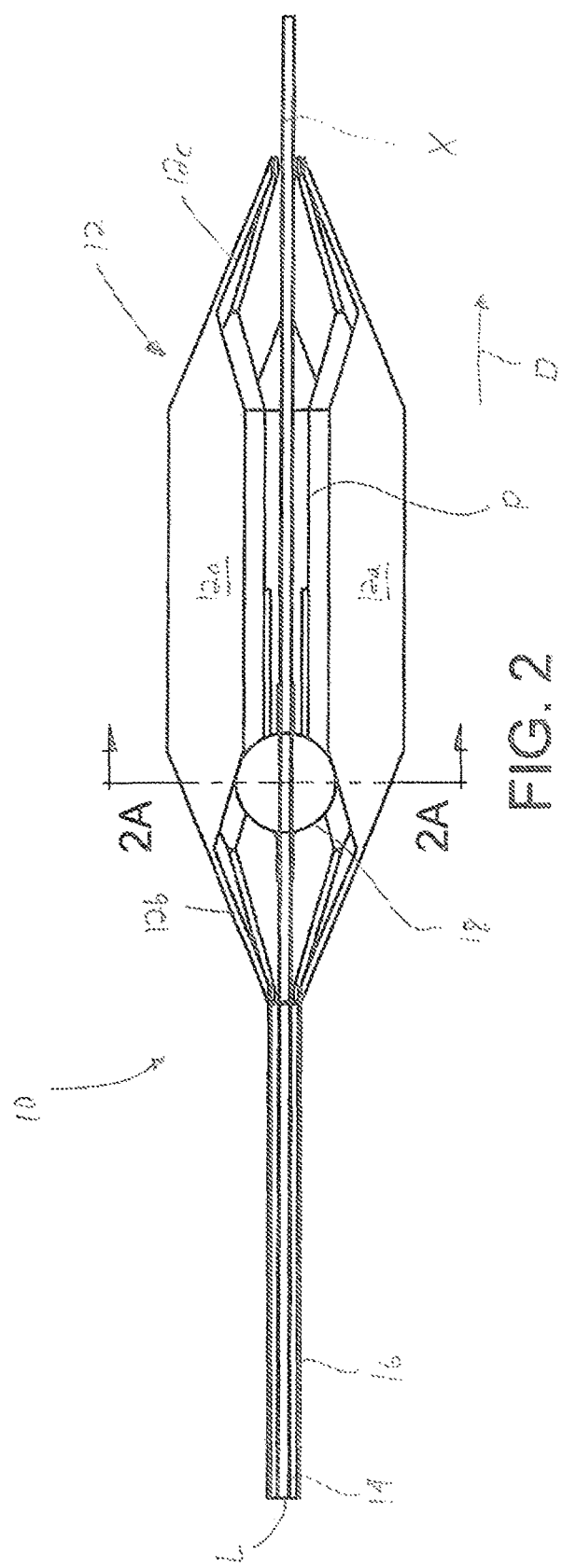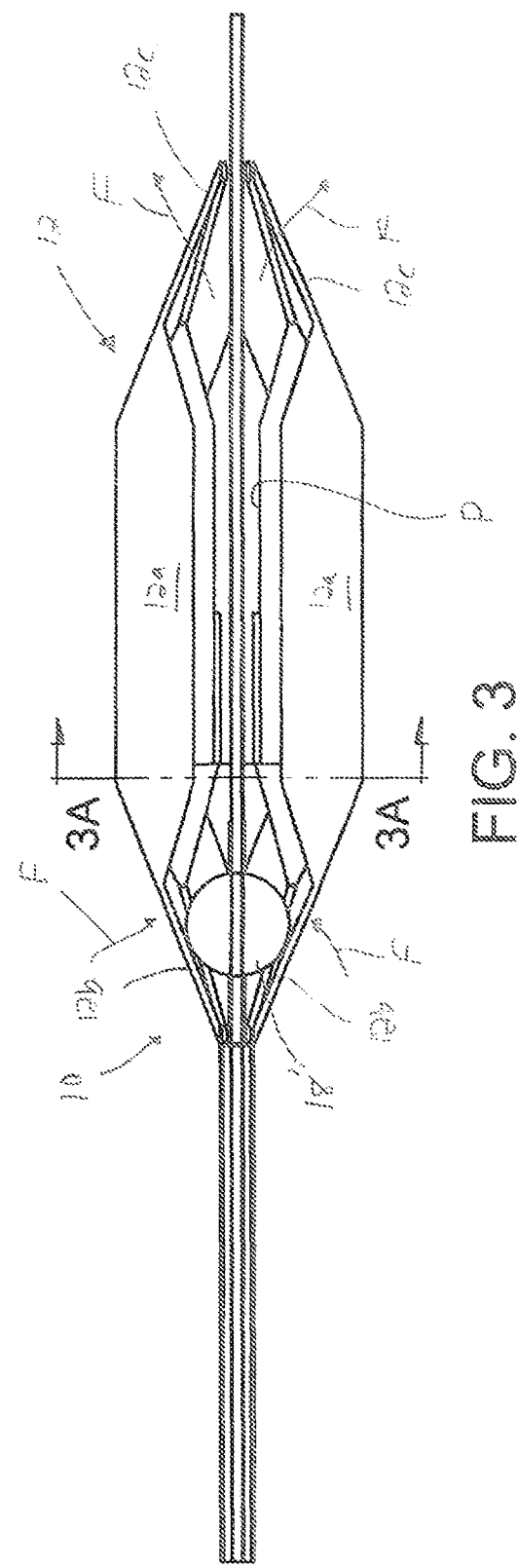

PERFUSION BALLOON WITH A SELECTIVELY ACTUATABLE VALVE

INCORPORATION BY REFERENCE

All publications and patent applications mentioned in this specification are herein incorporated by reference to the same extent as if each individual publication or patent application was specifically and individually indicated to be incorporated by reference.

BACKGROUND

Expandable devices, such as balloons, are widely used in medical procedures. In the case of a balloon, it is inserted, typically on the end of a catheter, until the balloon reaches the area of interest. Adding pressure to the balloon causes the balloon to inflate. In one variation of use, the balloon creates a space inside the body when the balloon inflates.

Balloons may be used in the valves associated with the heart, including during Balloon Aortic Valvuloplasty (BAV) (as described in Hara et al. "Percutaneous balloon aortic valvuloplasty revisited: time for a renaissance?" *Circulation* 2007; 115:e334-8) and Transcatheter Aortic Valve Implantation (TAVI). For such a procedure, the inflated balloon may be designed to allow for continued blood flow, or perfusion. However, when the balloon is inflated, the heart valve is necessarily temporarily disabled. This can lead to disruptions in the blood flow, including by creating undesirable back flow.

Thus, it would be desirable to provide a perfusion balloon that can be used to regulate the flow of fluid during a procedure in a selective manner, especially when used in connection with a procedure involving a valve that is disabled as a result of the procedure or otherwise.

SUMMARY OF THE DISCLOSURE

In general, a perfusion balloon including a selectively actuatable valve is proposed. More specifically, an inflatable perfusion balloon includes a passage for allowing fluid flow in an inflated condition of the balloon, and an inflatable valve that may be used to selectively block the passage.

According to a more specific aspect of the disclosure, an apparatus for performing a medical procedure in a vessel for transmitting a flow of fluid is provided. The apparatus comprises an inflatable perfusion balloon for permitting the fluid flow in the vessel while in an inflated condition. An inflatable valve is provided for controlling the fluid flow in the vessel, such as by regulating the flow of fluid through the perfusion balloon when inflated.

In one possible embodiment, the inflatable valve comprises a balloon associated with an internal passage of the perfusion balloon. The balloon may comprise a generally spherical balloon. A catheter shaft may be provided for supporting the perfusion balloon, the catheter shaft including at least one lumen for receiving a support, such as a guidewire tube having an inflation, for supporting the inflatable valve. In one particular embodiment, the inflatable valve is movable relative to the support between a first position substantially obstructing fluid flow and a second position allowing fluid flow.

Another aspect of the disclosure pertains to an apparatus for use in performing a medical procedure in a vessel for transmitting a fluid flow. The apparatus comprises a perfusion balloon including a passage associated with an opening for receiving the fluid flow within the vessel, and a valve selectively positionable within the passage for controlling the fluid flow.

In one embodiment, the valve comprises an inflatable balloon positioned in an internal passage of the perfusion balloon. The balloon may comprise a generally spherical balloon. A catheter shaft for supporting the perfusion balloon includes at least one lumen for receiving a support for supporting the inflatable valve. The valve may be movable between a first position substantially obstructing fluid flow through the passage and a second position allowing fluid flow through the passage.

In any embodiment, the perfusion balloon may comprise a plurality of cells in a single cross-section of the per balloon. Each cell includes a neck extending to a catheter shaft supporting the perfusion balloon, the necks together forming, a retainer for the inflatable valve. The retainer may be located at a proximal end portion of the perfusion balloon.

A further aspect of the disclosure pertains to an apparatus for use in performing a medical procedure in a vessel for transmitting a fluid flow. The apparatus comprises a first inflatable balloon including a passage for permitting the fluid flow in the vessel in an inflated condition, and a second inflatable balloon for controlling the fluid flow to the passage.

In one embodiment, a catheter shaft is provided for supporting the first inflatable balloon, the catheter shaft including a first tube having a first lumen in fluid communication with the first inflatable balloon and a second tube having a second lumen in fluid communication with the second inflatable balloon (such as part of a guidewire tube). The inflatable balloon may be movable between a first position substantially obstructing fluid flow through the passage and a second position allowing fluid flow through the passage, such as along an associated guidewire tube.

Another aspect of the disclosure pertains to an apparatus for use in performing a medical procedure in a vessel for transmitting a fluid flow. The apparatus comprises a support including an inflatable balloon adapted for sliding movement from a first proximal location to a second distal location. The support may comprise a tube including an inflation lumen for supplying a fluid to the balloon. The balloon may be generally spherical, and includes a proximal neck and a distal neck.

Still a further aspect of the invention pertains to an apparatus for use in performing a medical procedure in a vessel for transmitting a fluid flow. The apparatus comprises a balloon including a generally spherical inflatable body, a proximal neck, and a distal neck. The proximal neck and distal neck have generally circular cross sections. A support may also be provided for supporting the balloon, the support including an inflation lumen in fluid communication with the inflatable body. A perfusion balloon adapted for receiving the balloon may also be provided.

Yet another aspect of the disclosure pertains to an apparatus for use in performing a medical procedure in a vessel for transmitting a fluid flow, comprising a first inflatable balloon, a catheter shaft supporting the first inflatable balloon, the catheter shaft including a first lumen, and a guidewire tube positioned in the first lumen. The guidewire tube includes an inflation lumen for supplying an inflation fluid to the inflatable balloon and a guidewire lumen for receiving a guidewire.

In one embodiment, the catheter tube comprises a second lumen for supplying an inflation fluid to the first inflatable balloon. The apparatus may further include a second inflatable balloon in fluid communication with the inflation lumen of the guidewire tube. The first inflatable balloon may comprise a perfusion balloon and the second inflatable balloon is positioned within the perfusion balloon. The perfusion balloon may comprise a plurality of inflatable cells in a single cross-section of the balloon, each cell including a proximal neck in fluid communication with the first lumen. The first inflatable balloon may comprise a generally spherical balloon.

The disclosure also pertains to a method of performing a valvuloplasty using any disclosed apparatus. The method may include the steps of providing a perfusion balloon adjacent to the valve, the perfusion balloon including a passage for transmitting the flow of fluid, and providing a balloon to regulate the flow of fluid through the perfusion balloon. The method may further including the step of inflating the balloons.

BRIEF DESCRIPTION OF THE DRAWINGS

FIG. 2 is a cross-sectional side view of the device of FIG. 1 along line 2-2, with the inflatable valve in a first position for blocking flow through a central passage of the device;

FIG. 3 is a cross-sectional side view of the device of FIG. 1, with the inflatable valve in a second position for permitting flow through a central passage of the device;

DETAILED DESCRIPTION

The invention disclosed pertains to an inflatable device in the nature of a perfusion balloon. The novel features of the invention are set forth with particularity in the claims that follow. A better understanding of the features and advantages of the invention will be obtained by reference to the following detailed description that sets forth illustrative embodiments, in which the principles of the invention are utilized, and the accompanying drawings.

Figure 1:
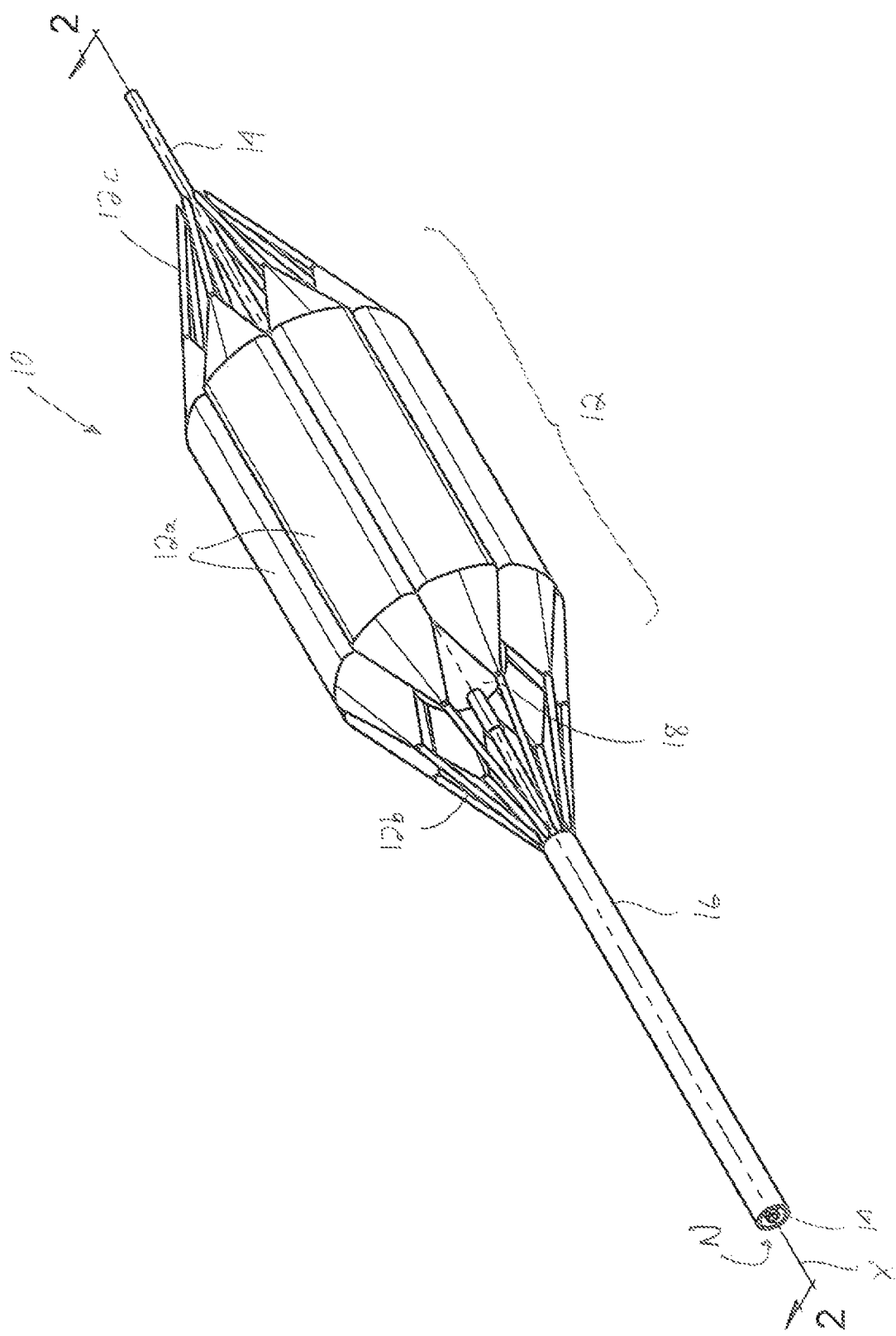
FIG. 1 is a schematic side view of an inflatable device in the expanded condition.

FIG. 1 shows an inflatable device 10 including a perfusion balloon 12 in an inflated condition, ready for use in connection with a procedure (but which balloon would normally be folded for purposes of delivery through the vasculature to a selected treatment area, such as the aortic valve). From viewing the inflated condition, it can be understood that the balloon 12 of the device 10 may have multiple inflatable cells 12a (eight shown, but any number may be provided) in at least a single cross-section of the balloon (see, e.g., FIGS. 2A and 3A). A retainer, such as a tubular, flexible sheath or covering (not shown), may be provided over the central portion of the cells 12a to retain them in a generally annular configuration in the illustrated embodiment, and may also serve to protect the cells when contact is made with a stenosed valve or the like.

The cells 12a may be individual or discrete, separately inflatable balloons. Each cell 12a having a separate inflation lumen via neck 12b, as noted, and also a neck 12c at the distal end, which may be sealed at a distal tip, or may be parts of a single balloon. The latter may be achieved by a segmented, elongated structure that is folded in a manner that causes the cells 12a to form a passage P extending along a central axis X, along which fluid such as blood may continue to flow, even when the balloon 12 is fully inflated (which may be done through a single inflation lumen, or each balloon could have its own inflation lumen). A full description of this type of balloon may be found in International Patent Application Publication No. WO201209997A1. However, other forms of perfusion balloons could also be used, such as for example a tubular balloon, one having a peripheral (e.g., helical) channel for purposes of allowing fluid flow to occur during inflation, or any combination of these technologies.

In any case, the device 10 may also include an inner shaft or tube 14 including an inflation lumen L extending along the central axis X. The inner tube 14 may form part of a catheter tube or shaft 16, which includes a lumen N in which the inner tube 14 is positioned. The perfusion balloon 12 may in turn be attached to the catheter shaft 16, such as at the proximal necks 12b forming the entrance to passage P, which may receive inflation fluid through the lumen N.

According to one aspect of the disclosure, a valve is provided for selectively regulating the flow of fluid through the passage P. In one embodiment, the valve comprises a selectively inflatable device, such as a balloon 18. The balloon 18 may be positioned within the passage P, such as at the open proximal end of it, in order to providing a one way valve function during the procedure.

The balloon 18 may be generally spherical in shape, but could also take other forms as well. The balloon 18 may be carried by a support for extending through the passage P without obstructing it, such as the guidewire tube 14, which support may be fixed or may be movable relative to the perfusion balloon 12. As discussed in further detail below, the guidewire tube 14 may include an inflation lumen L (see FIG. 2) for delivering the fluid for selectively inflating the balloon 18, which may also move relative to the underlying support (tube 14).

Figure 2A:
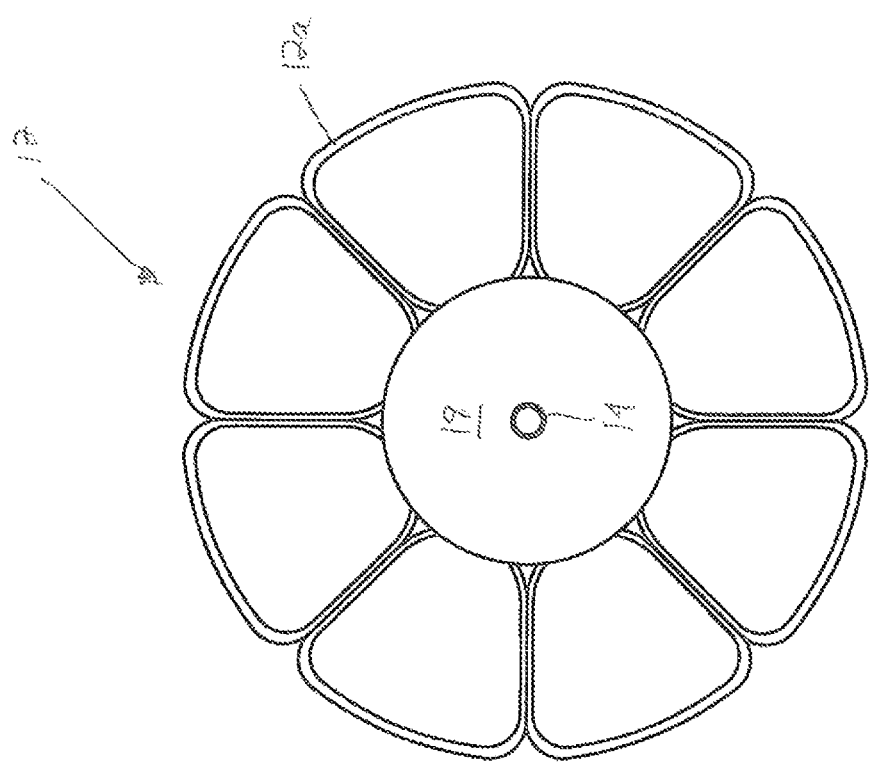
FIG. 2A is a cross-sectional view along line 2A-2A of FIG. 2.

Turning to FIGS. 2 and 2A, it can be seen that the balloon 18 when inflated and advanced in the distal direction D (opposite the proximal direction) is designed to regulate the flow of fluid. Specifically, the balloon 18 may substantially or completely obstruct the passage P, and thereby substantially or completely block fluid flow (thus, in this distal position corresponding to the closed position of the valve thus created). The movement of the balloon 18 to this position may be achieved by moving the associated support, such as guidewire tube 14, or may be done automatically as the result of varying fluid pressure created by flow in the vessel (such as the result of the pumping action of the heart moving blood) and passage P, in particular.

Figure 3A:
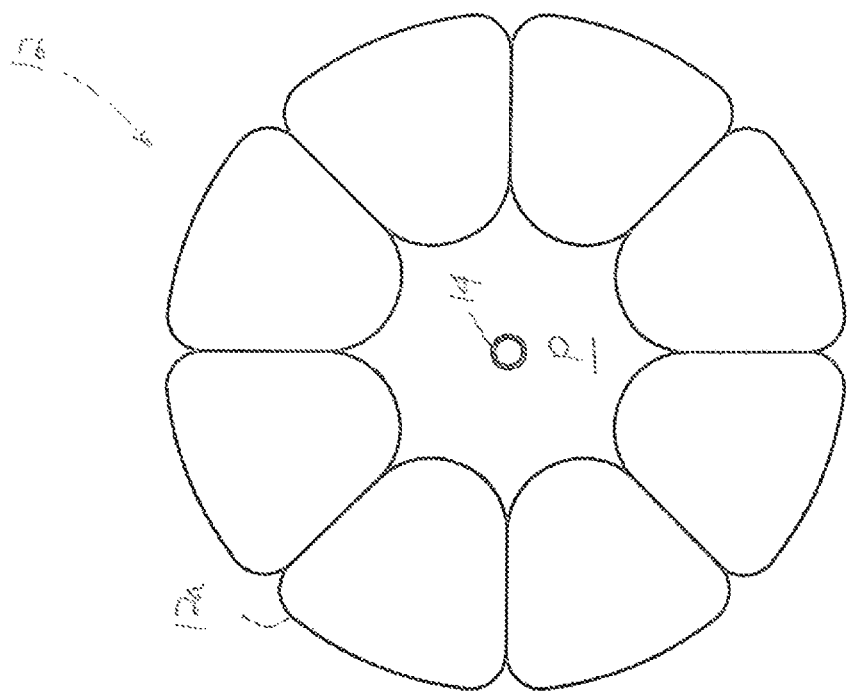
FIG. 3A is a cross-sectional view taken along line 3A-3A of FIG. 2.

As understood from FIGS. 3 and 3A, when the inflated balloon 18' is withdrawn from the passage P in the opposite (proximal) direction, fluid F may flow in the spaces between the proximal necks 12b associated with the individual cells 12a. As this proximal position corresponds to the open condition of the valve thus created, the fluid F may thus enter the passage P and ultimately perfuse through the balloon 12, exiting in the space(s) between the distal necks 12c and continuing on through the vessel (away from the heart, in the case of the aortic valve). In this condition, it can be appreciated that the necks 12b collectively form a retainer or cage for engaging the balloon 18 and precluding further movement in the proximal direction. Through selective actuation of the balloon 18 when inflated via the flow rhythms created by the beating heart, a one way valve results that can be used to mimic the natural flow created by the associated valve, which would be incapacitated as a result of the procedure.

Figure 4A:
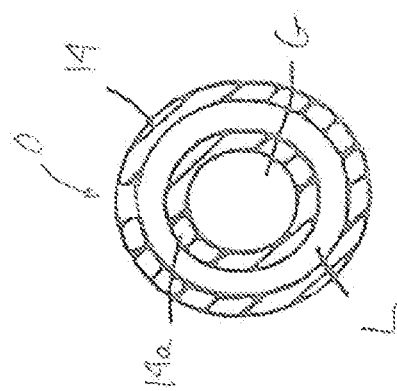
FIG. 4A is a partial cross-sectional view along line 4A-4A of FIG. 4.
Figure 4:
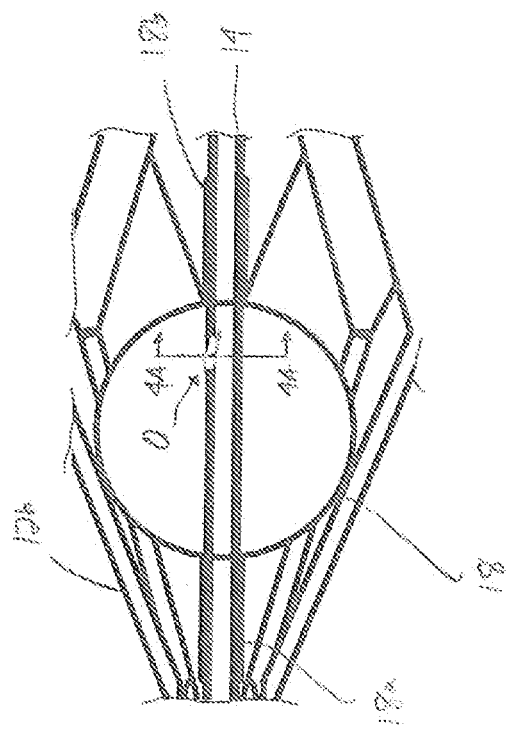
FIG. 4 is an enlarged, partially cutaway view of the inflatable valve in the second position

FIG. 4 illustrates one manner of selectively supplying inflation fluid to the balloon 18. As noted above, the guidewire tube 14 may be provided with inflation lumen L for communicating fluid to the interior of the balloon 18, such as via one or more openings O. Tubular extensions or necks 18a, 18b located proximal and distal of the balloon 18a connect to the corresponding proximal and distal ends of the inflatable spherical body. These necks 18a, 18b overlie the tube 14 and thrill seals for containing the inflation fluid within an interior inflatable compartment of the balloon 18, while at the same time permitting the sliding movement for achieving the selective regulation of flow by obstructing the passage P (or not). As can be appreciated, the necks 18a, 18b may be generally circular in cross-section, and may have an inner diameter that only slightly exceeds the outer diameter of the tube 14, which may thus form the fluid impervious seal. The necks 18a, 18b may be elongated in the direction of axis A, and as a result of the controlled sliding movement may enter the shaft 16 and the passage P at the proximal and distal ends, respectively (compare FIGS. 2 and 3).

Figure 5A:
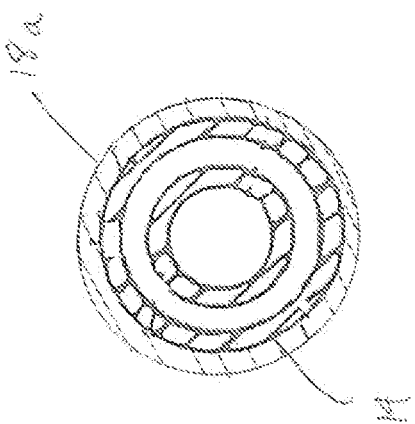
FIG. 5A is a partial cross-sectional view along line 5A-5A of FIG. 5.
Figure 5:
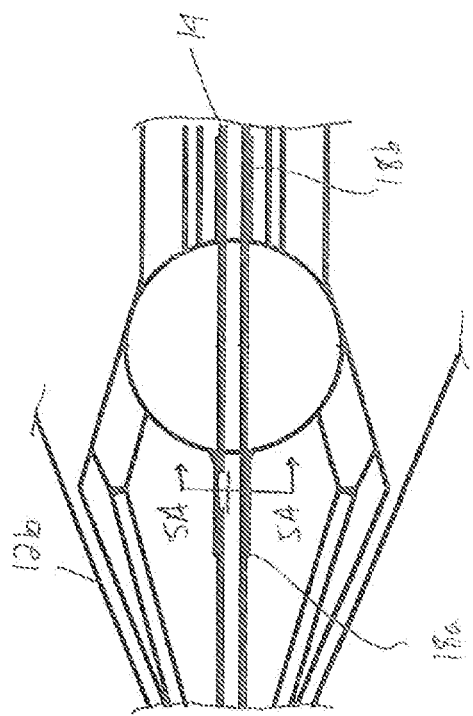
FIG. 5 is an enlarged partially cutaway view of the inflatable valve in the first position.

As can be appreciated by comparing FIGS. 4 and 4A with FIGS. 5 and 5A, the opening O may be arranged to communicate with the interior of the balloon 18 in one position (proximal), and then remain blocked by the extension (proximal extension 18a in this case) when the balloon moves to the other position (distal). The tube 14 may be coaxial, and include a guidewire lumen G formed by an inner tube 14a. The guidewire lumen G may extend the entire length of the tube 14 (whereas, the inflation lumen L may end at or near opening O).

Various materials may be used for forming the described structures, including as outlined in International Patent Application Publication No. WO2012099979A1. The balloon 18 may be made of a polyurethane material. Inflation of the balloon 18 may also be achieved using a separate device from the one used to inflate the perfusion balloon 12, which thereby allows for a manner of selective control of the valve this formed.

The foregoing discussion is intended to provide an illustration of the inventive concepts, and is not intended to limit the invention to any particular mode or form. Any elements described herein as singular can be pluralized (i.e., anything described as "one" can be more than one), and plural elements can be used individually. Characteristics disclosed of a single variation of an element, the device, the methods, or combinations thereof can be used or apply for other variations, for example, dimensions, burst pressures, shapes, materials, or combinations thereof. Any species element of a genus element can have the characteristics or elements of any other species element of that genus. Terms like "generally" or "substantially" mean that the value may vary depending on the circumstances, such as up to 10% of a given condition. The above-described configurations, elements or complete assemblies and methods and their elements for carrying out the invention, and variations of aspects of the invention can be combined and modified with each other in any combination, along with any obvious modifications.

The invention claimed is:

1. An apparatus for performing a medical procedure in a vessel for transmitting a flow of fluid, comprising:
    an inflatable perfusion balloon having a proximal end and including a passage having an opening adjacent the proximal end for permitting the fluid flow in the vessel while the perfusion balloon is in an inflated condition;
    an inflatable valve for controlling the fluid flow within the passage;
    a support for supporting the inflatable valve within the passage; and
    a catheter shaft for supporting the perfusion balloon and including an inflation lumen for the perfusion balloon, wherein the inflatable valve when inflated is slidable along the support between a first position substantially obstructing fluid flow within the passage from the opening and a second position allowing fluid flow within the passage from the opening.

2. The apparatus of claim 1, wherein the inflatable valve comprises a balloon.

3. The apparatus of claim 2, wherein the balloon comprises a generally spherical balloon.

4. The apparatus of claim 1, wherein the support comprises a tube including a second inflation lumen for the inflatable valve.

5. The apparatus of claim 1, wherein the perfusion balloon comprises a plurality of cells in a single cross-section of the perfusion balloon.

6. The apparatus of claim 5, wherein each cell includes a tubular neck extending to the catheter shaft supporting the perfusion balloon and supplying inflation fluid to the cell to which the tubular neck is connected, the tubular necks together forming a retainer for the inflatable valve.

7. The apparatus of claim 1, further including a retainer for retaining the inflatable valve in the passage of the perfusion balloon.

8. An apparatus for use in performing a medical procedure in a vessel for transmitting a fluid flow, comprising:
    a perfusion balloon having a proximal end and including a passage associated with an opening adjacent the proximal end for receiving the fluid flow within the vessel;
    a shaft including at least one inflation lumen for supplying an inflation fluid to the perfusion balloon;
    a valve selectively positionable within the passage for controlling the fluid flow; and
    wherein the valve is movable along a portion of the shaft within the passage between a first position substantially obstructing fluid flow from the opening to the passage and a second position allowing fluid flow from the opening to the passage.

9. The apparatus of claim 8, wherein the valve comprises an inflatable balloon positioned in an internal passage of the perfusion balloon.

10. The apparatus of claim 9, wherein the inflatable balloon comprises a generally spherical balloon.

11. The apparatus of claim 10, wherein each cell includes a tubular neck extending to a catheter shaft supporting the perfusion balloon and supplying inflation fluid to the cell to which the tubular neck is connected, the tubular necks together forming a retainer for the inflatable valve.

12. The apparatus of claim 11, wherein the retainer forms a proximal end portion of the perfusion balloon.

13. The apparatus of claim 8, further including a support tube for supporting the inflatable valve on the shaft.

14. The apparatus of claim 8, wherein the perfusion balloon comprises a plurality of cells in a single cross-section of the perfusion balloon.

15. An apparatus for use in performing a medical procedure in a vessel, comprising:
- a first inflatable balloon having a proximal end and including an opening adjacent the proximal end and a passage for transmitting a flow of fluid in an inflated condition;
- a second inflatable balloon for controlling the flow of fluid through the passage, the second inflatable balloon when inflated being movable from a first position substantially obstructing fluid flow through the passage to a second position allowing fluid flow through the passage; and
- a catheter shaft fixed to the first inflatable balloon, the catheter shaft including a first lumen in fluid communication with the first inflatable balloon and a second lumen in fluid communication with the second inflatable balloon.

16. The apparatus of claim 15, wherein the second inflatable balloon is movable within the first inflatable balloon along a guidewire tube from a first position substantially obstructing fluid flow through the passage to a second position allowing fluid flow through the passage.

17. The apparatus of claim 15, wherein the first balloon comprises a plurality of cells in a single cross-section of the balloon.

18. The apparatus of claim 15, wherein the second balloon comprises a generally spherical balloon.

19. The apparatus of claim 8, further including a retainer for retaining the inflatable valve in the passage of the perfusion balloon.

20. An apparatus for performing a medical procedure in a vessel for transmitting a flow of fluid, comprising:
- an inflatable perfusion balloon for permitting the fluid flow in the vessel while the perfusion balloon is in an inflated condition;
- an inflatable valve for controlling the fluid flow;
- a support for supporting the inflatable valve; and
- a catheter shaft for supporting the perfusion balloon and including an inflation lumen for the perfusion balloon, the catheter shaft further including at least one lumen for receiving the support for supporting the inflatable valve, wherein the inflatable valve when inflated is movable relative to the catheter shaft between a first position substantially obstructing fluid flow and a second position allowing fluid flow;
- wherein the perfusion balloon comprises a plurality of cells in a single cross-section of the perfusion balloon;
- wherein each cell includes a tubular neck extending to the catheter shaft supporting the perfusion balloon and supplying inflation fluid to the cell to which the tubular neck is connected, the tubular necks together forming a retainer for the inflatable valve.

* * * * *